United States Patent [19]

Buzzetti et al.

[11] Patent Number: 4,904,650
[45] Date of Patent: * Feb. 27, 1990

[54] SUBSTITUTED ANDROSTA-1,4-DIENE-3,17-DIONES

[75] Inventors: Franco Buzzetti, Monza; Natale Barbugian, Milan; Paolo Lombardi, Milan; Enrico di Salle, Milan, all of Italy

[73] Assignee: Farmitalia Carlo Erba S.p.A., Milan, Italy

[*] Notice: The portion of the term of this patent subsequent to Feb. 28, 2006 has been disclaimed.

[21] Appl. No.: 225,674

[22] Filed: Jul. 26, 1988

Related U.S. Application Data

[62] Division of Ser. No. 882,364, Jul. 7, 1986, Pat. No. 4,808,616.

[30] Foreign Application Priority Data

Jul. 9, 1985 [GB] United Kingdom ............... 8517360

[51] Int. Cl.$^4$ .......................... A61K 31/56; C07J 9/00
[52] U.S. Cl. .................................. 514/177; 260/397.3
[58] Field of Search ...................... 260/397.3; 514/177

[56] References Cited

U.S. PATENT DOCUMENTS

| | | | |
|---|---|---|---|
| 2,744,120 | 5/1956 | Fried et al. | |
| 3,112,305 | 11/1963 | Kirk et al. | 260/397.3 |
| 4,235,893 | 11/1980 | Brodie et al. | |
| 4,322,349 | 3/1982 | Annen et al. | 260/397.3 |
| 4,512,986 | 4/1985 | Reel et al. | 260/397.3 |
| 4,591,585 | 5/1986 | Kerb et al. | 514/177 |
| 4,808,616 | 2/1989 | Buzzetti et al. | 514/177 |

FOREIGN PATENT DOCUMENTS

| | | |
|---|---|---|
| 1042291 | 11/1961 | United Kingdom . |
| 929985 | 6/1963 | United Kingdom . |
| 1263992 | 2/1972 | United Kingdom . |

OTHER PUBLICATIONS

"Aromatase Inhibitors, Synthesis and Biological Activity of Androstenedione Derivatives", David A. Marsh et al., J. Med. Chem., 1985, pp. 788–795.
Brodie, A., "Overview of Recent Developments of Aromatase Inhibitors", Cancer Research, (Suppl.) 42,3312s–3314, Aug. 1982.
Covey, et al., "A New Hypothesis Based on Suicide Substrate . . . ", Cancer Research, (Suppl.) 42, 3327s–3333s, Aug. 1982.
Farmdoc Abstract U.S. 4289–762 RICH 27 06 80.
Farmdoc Abstract U.S. patent 4322–416.
Metcalf et al., "Substrate-Induced Inactivation of Aromatase . . . ", J. Am. Chem. Soc., 1981, 103, 3221–3222.
Derwent Publications Ltd., EP 100 566A.
Farmdoc Abstract GB 2100–60.
Chemical Abstracts U.S. 3,117,966, (Petrow), vol. 60, 9336.
Chemical Abstracts, U.S. 3,112,305, vol. 60, 9337.
Farmdoc Abstract, SA 65/4327.
Farmdoc Abstract, U.S. 3,356,694.
Korp et al., "Efficient Synthesis and Mechanisms of Formation . . . ", J.C.S. Chem. Comm., 1973, pp. 72–73.
Schering AG, "New 1-Alky-Androsta-1,4-Diene-3,1-7-Dione . . . ", Pharmaceuticals, p. 9.
Petrow et al., "Prostatic Cancer-II, . . . ", Chemical Abstracts, vol. 101, 1984, p. 84.
Derwent Abstracts of Belgian patent 816,364.
Derwent Abstract of German patent 3422–187-A.

Primary Examiner—Joseph A. Lipovsky
Attorney, Agent, or Firm—Armstrong, Nikaido, Marmelstein, Kubovcik & Murray

[57] ABSTRACT

The invention relates to 6-alkylidenadrosta-1,4-diene-3,17-dione derivatives, having the following general formula

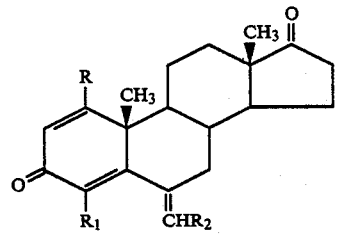

wherein
each of R and $R_2$, independently, is hydrogen or $C_1$–$C_6$ alkyl and $R_1$ is hydrogen, halogen or $C_1$–$C_6$ alkyl, which are useful in therapy, in particular in the treatment of hormone-dependent cancers.

8 Claims, No Drawings

SUBSTITUTED ANDROSTA-1,4-DIENE-3,17-DIONES

This is a division, of application Ser. No. 882,364 filed July 7, 1986 now U.S. Pat. No. 4,808,616.

The present invention relates to novel 6-alkylidenandrosta-1,4-diene-3,17-dione derivatives, to a process for their preparation, to pharmaceutical compositions containing them, and to the use of said compounds for the treatment of hormone-dependent cancers in mammals. Basic and clinical data indicate that aromatized metabolites of androgens, i.e. the estrogens, are the hormones involved in the pathogenic cellular changes associated with the growth of some hormone-dependent cancers, such as breast, endometrial and ovarian carcinomas.

Estrogens are also involved in the pathogenesis of benign prostatic hyperplasia.

Endogenous estrogens are ultimately formed from either androstenedione or testosterone as immediate precursors. The reaction of central importance is the aromatization of the steroidic ring A, which is performed by the enzyme aromatase. As aromatization is a unique reaction and the last in the series of steps in the biosynthesis of estrogens, it has been envisaged that an effective inhibition of the aromatase, resulting from compounds able to interact with the aromatizing steps, may have useful application for controlling the amount of circulating estrogens, estrogen-dependent processes in reproduction, and estrogen-dependent tumours.

Known steroidal substances which have been reported to be endowed with an aromatase-inhibiting action are, for example, $\Delta^1$-testololactone [U.S. Pat. No. 2,744,120], 4-hydroxyandrost-4-ene-3,17-dione and esters thereof [see, for example, U.S. Pat. No. 4,235,893], 10-(1,2-propadienyl)-estr-4-ene-3,17-dione [U.S. Pat. No. 4,289,762], 10-(2-propynyl)-estr-4-ene-3,17-dione [J. Am. Chem. Soc., 103, 3221 (1981) and U.S. Pat. No. 4,322,416], 19-thioandrostene derivatives (Europ. Pat. Appl. 100566), androsta-4,6-diene-3,17-dione, androsta-1,4,6-triene-3,17-dione [G.B. Pat. Appl. 2,100,601A] and androsta-1,4-diene-3,17-dione [Cancer Res. (Suppl.) 42, 3327 (1982)].

The novel compounds of the present invention, besides exhibiting a potent in vitro inhibition of the aromatase, are endowed with a superior in vivo potency by virtue of their better metabolic stability when compared to the compounds of the previous art.

The present invention provides compounds having the following general formula (I)

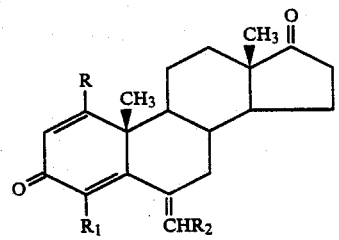

wherein
each of R and $R_2$, independently, is hydrogen or $C_1$–$C_6$ alkyl and $R_1$ is hydrogen, halogen or $C_1$–$C_6$ alkyl.

The formula reported above for the compounds of the invention includes all the possible isomers, in particular Z and E isomers, both separately and as mixture, of the compounds of formula (I) in which $R_2$ is $C_1$–$C_6$ alkyl. In the formulae of this specification the broken lines (||||||||) indicate that the substituents are in the α-configuration, i.e. below the plane of the ring, while the heavy solid lines (▬) indicate that the substituents are in the β-configuration, i.e. above the plane of the ring; the wavy lines (∼∼∼) indicate that the groups may be both in the α-configuration or in the β-configuration.

A $C_1$–$C_6$ alkyl group is preferably a $C_1$–$C_4$ alkyl group, in particular methyl, ethyl, propyl or t-butyl, more preferably methyl or ethyl. From these examples it appears clear that an alkyl radical may be a branched or straight chain group. A halogen atom is e.g. chlorine, fluorine, bromine, in particular chlorine and fluorine, more preferably fluorine.

Preferred compounds of the invention are the compounds of formula (I), wherein
R is hydrogen or $C_1$–$C_4$ alkyl
$R_1$ is hydrogen, fluorine, chlorine or $C_1$–$C_4$ alkyl and
$R_2$ is hydrogen or $C_1$–$C_4$ alkyl. More preferred compounds of the invention are the compounds of formula (I), wherein
R is hydrogen, methyl or ethyl;
$R_1$ is hydrogen, fluorine or chlorine and
$R_2$ is hydrogen.

Examples of specific compounds of the invention are:
6-methylenandrosta-1,4-diene-3,17-dione;
1-methyl-6-methylenandrosta-1,4-diene-3,17-dione;
1-ethyl-6-methylenandrosta-1,4-diene-3,17-dione;
4-methyl-6-methylenandrosta-1,4-diene-3,17-dione;
4-ethyl-6-methylenandrosta-1,4-diene-3,17-dione;
4-fluoro-6-methylenandrosta-1,4-diene-3,17-dione;
4-chloro-6-methylenandrosta-1,4-diene-3,17-dione;
6-ethylidenandrosta-1,4-diene-3,17-dione;
6-propylidenandrosta-1,4-diene-3,17-dione;
4-fluoro-1-methyl-6-methylenandrosta-1,4-diene-3,17-dione;
4-chloro-1-methyl-6-methylenandrosta-1,4-diene-3,17-dione;
1-methyl-6-ethylidenandrosta-1,4-diene-3,17-dione; and
4-fluoro-6-ethylidenandrosta-1,4-diene-3,17-dione.

The compounds of the invention can be obtained by a process comprising:

(a) dehydrogenating a compound of formula (II)

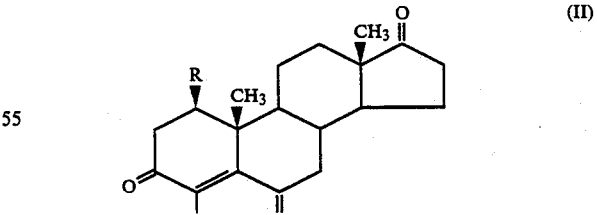

wherein
$R_a$ is hydrogen or $C_1$–$C_6$ alkyl and R and $R_2$ are as defined above, thus obtaining a compound of formula (I) in which
$R_1$ is hydrogen or $C_1$–$C_6$ alkyl and R and $R_2$ are as defined above; or (b) reacting a compound of formula (III)

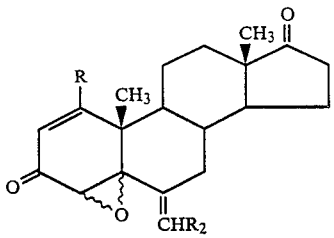

(III)

wherein
R and R$_2$ are as defined above, with a hydro-halogenating agent, thus obtaining a compound of formula (I) wherein R$_1$ is halogen and R and R$_2$ are as defined above; and, if desired separating a mixture of isomers of compounds of formula (I) into the single isomers.

The dehydrogenation of a compound of formula (II) may be carried out by treatment with a suitable dehydrogenating agent, e.g. dichlorodicyanobenzoquinone (DDQ), selenium dioxide or chloranil. Preferably such reaction is performed by treatment with DDQ, in an inert solvent, such as dioxane, benzene, toluene or dichloromethane, at a temperature ranging from about 40° C. to about 120° C. and reaction times ranging from about 12 hours to about 72 hours.

The hydro-halogenating agent which reacts with a compound of formula (III) is e.g. a hydrohalic acid or a trihaloborane. The reaction of a compound of formula (III) with a hydrohalic acid or a trihaloborane may be carried out according to known methods, e.g. Camerino et al, 1956, Il Farmaco 11, 586 and A. Bowers et al., 1958, Tetrahedron 3, 14, respectively.

When the hydrohalic acid is the hydrochloric or hydrobromic one, such reaction is preferably performed in acetic acid or ethanol, at a temperature ranging from about 0° C. to about 100° C.

When a trihaloborane is used, e.g. boron trifluoride, the reaction is preferably performed in an inert solvent, such as diethyl ether, benzene or dichloromethane, at a temperature ranging from about −30° C. to about 50° C.

The separation of a mixture of isomers of a compound of formula (I) may be carried out according to conventional methods known per se.

For example the separation of a mixture of geometric isomers may be performed by fractional crystallization or by separation through column chromatography.

Compounds of formula (II) in which R$_a$ is hydrogen, R is C$_1$-C$_6$ alkyl and R$_2$ is as defined above may be synthesized according to the following reaction scheme by using methods known per se:

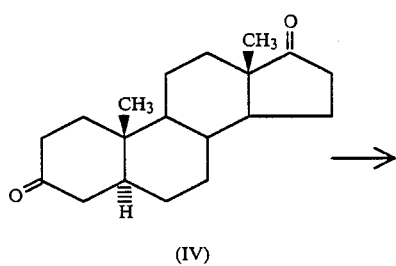

(IV)

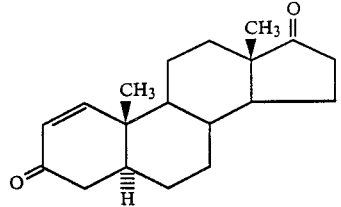

(V)

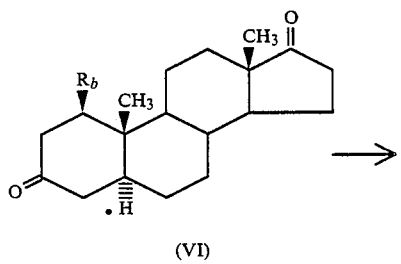

(VI)

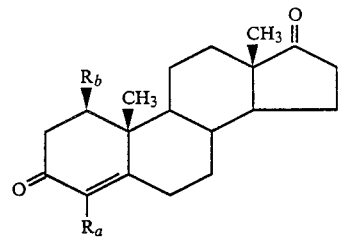

(VII)

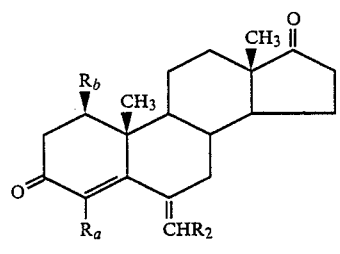

(II)

wherein R$_b$ is C$_1$-C$_6$ alkyl, R$_a$ is hydrogen and R$_2$ is as defined above.

For example, dehydrogenation of compound of formula (IV) to obtain compound of formula (V) may be performed e.g. according to H. J. Ringold et al. 1962, Chemistry and Industry, 211. Preferably it is carried out by treatment with DDQ in boiling dioxane.

A compound of formula (VI) is obtained by alkylating a compound of formula (V), e.g. according to known procedures. Preferably the alkylation is performed by adding the compound of formula (V), dissolved in an inert solvent, to a solution of dialkyllithium copper in the same or different inert solvent. Suitable inert solvents are e.g. methylene chloride, tetrahydrofurane, benzene or diethyl ether, the last one being the preferred. The reaction is preferably performed at temperatures varying from about −75° C. to about 20° C., with a temperature range from about −5° C. to about 0°

C. being the preferred. The ratio of reagents is not critical but at least 2 moles of dialkyllithium copper are to be present. Noteworthy is that the addition occurs selectively on the β-face; consequently in the 1-position there is an axial hydrogen atom suitable for elimination. A compound of formula (VII) may be obtained starting from a compound of formula (VI) according to known methods, e.g. M. Mori, 1962, Chem. Pharm. Bull. (Tokio), 10, 386. Hence a compound of formula (VI) may be brominated by treatment with 1–1.2 equivalents of bromine in acetic acid, or other suitable solvents, at a temperature ranging from about 0° C. to about 50° C., preferably at room temperature, thus obtaining a 4-bromo-derivative which is then dehydrobrominated, without purification, in dimethylformamide solution in the presence of lithium chloride at about 140°–150° C. A compound of formula (II) may be obtained starting from a compound of formula (VII), according to known methods, e.g. according to the method of K. Annen, 1982, Synthesis, 34. Preferably a compound of formula (VII) is reacted with unsubstituted or appropriately $C_1-C_6$ alkyl substituted formaldehyde-diethylacetal in refluxing chloroform, in the presence of phosphoryl chloride and sodium acetate. Alternatively the same reaction may be carried out in other inert solvents, e.g. 1,2-dichloroethane, diethylether or dioxane, and in the presence of other suitable condensing agents, e.g. phosphorus pentoxide or p-toluenesulfonic acid.

Compounds of formula (II) in which $R_a$ is hydrogen, $R_b$ is hydrogen and $R_2$ are as defined above, may be obtained starting from the commercially available androst-4-ene-3,17-dione by using the same procedures described above for obtaining a compound of formula (II) starting from a compound of formula (VII).

Compounds of formula (II) in which $R_a$ is $C_1-C_6$ alkyl and R and $R_2$ are as defined above may be obtained according to known procedures, for example as shown in the following reaction scheme:

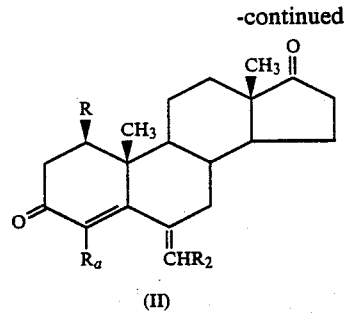
(II)

Alkylation of a compound of formula (VIII), i.e. androst-4-ene-3,17-dione and its 1-alkyl derivatives, using Atwater's procedure [N. W. Atwater, JACS 79, 5315 (1957)] of adding alkylchloride slowly to a refluxing solution of the ketone in t-butanol containing only a small excess of potassium t-butoxide produces a compound of formula (IX), i.e. 4-alkylandrost-4-ene-3,17-dione and its 1-alkyl derivatives, respectively.

Alternatively, the androst-4-ene-3,17-dione and its 1-alkyl derivative can be selectively thiomethylated at position 4 with formaldehyde and a thiol under basic conditions. Benzylmercaptan is the preferred thiol.

Desulphurization of the intermediate 4-thioether leads to the 4-methylandrost-4-ene-3,17-dione and its 1-alkyl analogues, respectively.

The introduction of an alkylidene group at position 6 into the compounds of formula (IX) can be accomplished according to the previously described method (K. Annen et al., Synthesis 1982, 34).

Compounds of formula (III) may be obtained according to known procedures, for example as shown in the following reaction scheme:

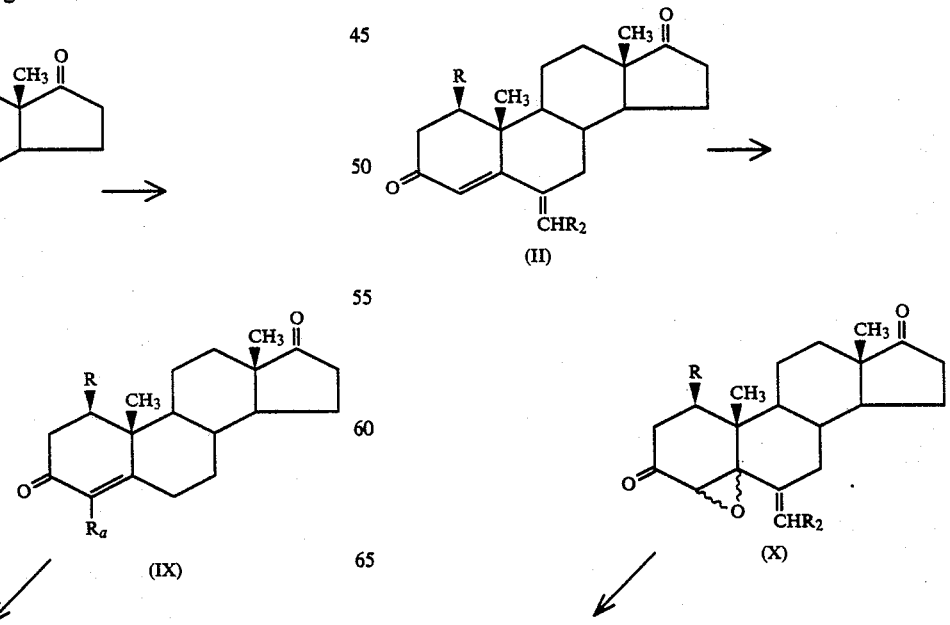

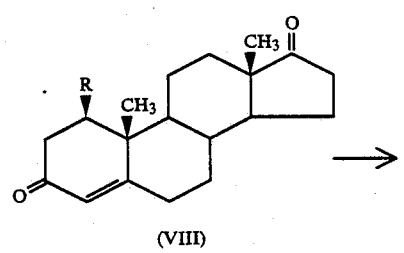
(IX)

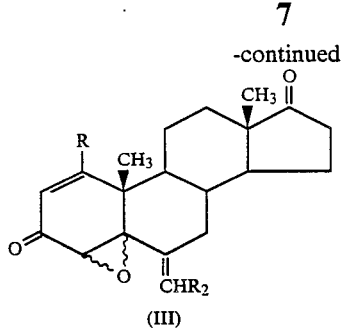

(III)

Epoxidation of a compound of formula (II) to obtain a compound of formula (X) may be carried out by treatment with a suitable oxidizing agent, preferably concentrated, e.g. 36% H₂O₂, in alcoholic alkali hydroxide solution, preferably KOH or NaOH in methanol, at a temperature ranging from 0° to 25° C. for from about 2 hours to several days. Dehydrogenation of a compound of formula (X) to obtain a compound of formula (III) may be carried out by treatment with a suitable dehydrogenating agent, e.g. with dichlorodicyano benzoquinone in a refluxing solvent as described above.

The compounds of formula (IV) and those of formula (VIII) in which R is hydrogen are known compounds.

The compounds of formula (VIII) in which R is $C_1$-$C_6$ alkyl are compounds of formula (VII), which may be obtained as described above.

The compounds of the present invention are inhibitors of the biotransformation of endogenous androgens, i.e. they are steroidal aromatase inhibitors.

Hence the compounds of the invention can be useful as an alternative to endocrine ablation, e.g. oophorectomy, hypophysectomy or adrenalectomy, in the treatment of advanced hormone-dependent breast, pancreatic, endometrial and ovarian cancers.

The aromatase inhibitors of formula (I) find also use in the control of reproduction: indeed a decrease in oestrogen levels in vivo results in gonad-inhibiting activity and in insufficient uterine development; aromatase inhibitors may be at the same time implantation inhibitors. Another application of the compounds of the invention is in the treatment of prostatic hypertrophy or hyperplasia, related to an excessive oestrogen production and the shifting of the oestrogen/androgen ratio to higher values. Aromatase inhibition by the compounds of the present invention was determined e.g. both in vitro (human placental aromatase) and in vivo (ovarian aromatase activity) in rats.

As an example, the activity of 6-methylenandrosta-1,4-diene-3,17-dione (internal code FCE 24304) was compared to that of well-known aromatase inhibitors: 4-hydroxy-androst-4-ene-3,17-dione (4OH-A), Δ¹-testololactone and androsta-1,4-diene-3,17-dione [A. M. H. Brodie, Cancer Research (Suppl.) 42, 3312 s, (1982); D. F. Covey and W. F. Hood, Cancer Research (Suppl.) 42, 3327 s, (1982)] and 6-methylenandrost-4-ene-3,17-dione which is disclosed by British Patent No. 929,985 as a convenient intermediate for the preparation of therapeutically valuable 6α-methyl steroidal hormones; however no therapeutical utility is attributed to said compound in the above British patent.

(a) Aromatase inhibition in vitro

The enzyme system was isolated from the microsomal fraction of human placental tissue according to standard procedure. The assay of Thompson and Siiteri [E. A. Thompson and P. K. Siiteri, J. Biol. Chem. 249, 5364, (1974)] which determines the rate of aromatization as measured by the liberation of ³H₂O from 4-[1β,2β-³H]androstene-3,17-dione was used. All incubations were carried out in a shaking water bath at 37° C. in air in 10 mM potassium phosphate buffer, pH 7.5, which contained 100 mM KCl, 1 mM EDA and 1 mM dithiothreitol. The experiments were carried out in 1 ml incubation volume containing 50 nM

4-[³H]

androstenedione, various concentrations of the inhibitors, 100 μM NADPH and 0.05 mg of microsomal proteins. After 15 minutes of incubation the reaction was stopped by the addition of chloroform (5 ml). After centrifugation at 1500×g for 5 min aliquots (0.5 ml) were removed from the water phase for determination of ³H₂O formed. The concentration of each compound required to reduce control aromatase by 50% ($IC_{50}$) was determined by plotting % inhibition versus log of inhibitor concentration.

The relative potency of each compound versus 4 OH—A was calculated according to the relation:

$$\text{Relative potency} = \frac{IC_{50} \text{ of 4 OH}-A}{IC_{50} \text{ of test compound}}$$

(b) Aromatase inhibition in vivo in rats

Adult female rats were twice treated subcutaneously with 100 I.U. pregnant mares' serum gonadotropin (PMSG) at 4 days' interval, in order to increase ovarian aromatase activity, according to Brodie's procedure [A. M. H. Brodie et al., Steroids 38, 693, (1981)]. Three days after the second PMSG treatment, groups of 6 animals each were given orally the vehicle (0.5% methocel) or the inhibitor at 30 mg/kg. Animals were killed 24 hrs later, microsomes were isolated from ovaries and their aromatase activity determined using a method similar to that described in (a). The incubations were carried out for 30 min in 1 ml incubation volume containing 0.1 mg of microsomal proteins, 100 nM

4-[³H]

androstenedione and 100 μM NADPH. % Inhibition of control aromatase activity was calculated.

TABLE

Inhibition of human placental aromatase in vitro and of rat ovarian aromatase in vivo

| Compound | IN VITRO | | IN VIVO |
|---|---|---|---|
| | $IC_{50}$ nM | (Relative potency) | % Aromatase inhibition at 30 mg/kg p.o. |
| 4-hydroxy-androst-4-ene-3,17-dione | 44 | (1.00) by definition | inactive |
| Δ¹-testololactone (testolactone) | 8240 | (0.005) | inactive |
| 6-methylenandrost-4-ene-3,17-dione | 74 | (0.59) | inactive |
| androsta-1, 4-diene-3,17-dione | 112 | (0.39) | 37 |
| 6-methylenandrosta-1,4-diene-3,17-dione (FCE 24304) | 39 | (1.13) | 81 |

From the results reported in the table it is evident that the new compound 6-methylenandrosta-1,4-diene-3,17- dione (FCE 24304) is a very potent aromatase inhibitor both "in vitro" and "in vivo".

In vitro the new compound FCE 24304 is about 3 times more potent than the related androsta-1,4-diene-3,17-dione and two hundred times more potent than $\Delta^1$-testololactone.

Although its in vitro potency is only slightly higher than that of 4-OH—A, the new compound is very effective when administered in vivo by oral route, as a consequence of an unusual resistance to epatic metabolization, while 4-OH—A is ineffective.

In fact, the major disadvantage for the therapeutical use of 4-OH—A as antitumor agent in women is the need of parenteral administration, the compound being extensively conjugated after oral administration [R. C. Coombes et al., Lancet II, 1237, (1984)].

In view of their high therapeutic index, the compounds of the invention can be used safely in medicine. For example, the approximate acute toxicity ($LD_{50}$) of the compounds of the invention in the mouse, determined by single administration of increasing doses and measured on the seventh day after the treatment was found to be negligible.

The compounds of the invention can be administered in a variety of dosage forms, e.g. orally, in the form of tablets, capsules, sugar or film coated tablets, liquid solutions or suspensions; rectally, in the form of suppositories; parenterally, e.g. intramuscularly, or by intravenous injection or infusion.

The dosage depends on the age, weight, conditions of the patient and administration route; for example the dosage adopted for oral administration to adult humans e.g. for the representative compound of the invention FCE 24304 may range from about 10 to about 150–200 mg pro dose, from 1 to 5 times daily.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

The solution for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The following examples illustrate but do not limit the invention.

EXAMPLE 1

0.50 g of 6-methylenandrost-4-ene-3,17-dione and 0.57 g of dichlorodicyanobenzoquinone were refluxed in 20 ml of anhydrous dioxane for about 15 hours. To remove the DDQ the suspension was filtered through alumina. After evaporation of the solvent the residue was dissolved in ethyl acetate, the organic layer washed with water, dried over sodium sulfate and the solvent removed under vacuum. The crude product was chromatographed on silica gel using hexane/ethyl acetate 40% to yield 0.25 g of pure 6-methylenandrosta-1,4-diene-3,17-dione, m.p. 188°–191° C., $\lambda_{max}$ 247 m$\mu$ ($\epsilon$ 13.750).

Found: C 81.01, H 8.05. $C_{20}H_{24}O_2$ requires: C 81.04, H 8.16.

Following the above described procedure the following compounds can be prepared:
1-methyl-6-methylenandrosta-1,4-diene-3,17-dione,
Found: C 81.18; H 8.37. $C_{21}H_{26}O_2$ requires: C 81.25; H 8.44;
1-ethyl-6-methylenandrosta-1,4-diene-3,17-dione,
Found: C 81.32; H 8.62. $C_{22}H_{28}O_2$ requires: C 81.44; H 8.70;
4-methyl-6-methylenandrosta-1,4-diene-3,17-dione,
Found: C 81.15; H 8.32. $C_{21}H_{26}O_2$ requires: C 81.25; H 8.44;
4-ethyl-6-methylenandrosta-1,4-diene-3,17-dione;
6-ethylidenandrosta-1,4-diene-3,17-dione;
6-propylidenandrosta-1,4-diene-3,17-dione, and
1-methyl-6-ethylidenandrosta-1,4-diene-3,17-dione.

EXAMPLE 2

A mixture of 6-methylenandrost-4-ene-3,17-dione (0.50 g), selenium dioxide (0.50 g) and t-butylalcohol (200 ml) was heated to reflux under nitrogen for about 30 hours. The cooled solution was filtered and then evaporated to dryness under reduced pressure. The residue was taken up in ethyl acetate (100 ml), treated with charcoal and washed consecutively with water, ammonium sulfide solution, cold 17% ammonium hydroxide, cold dilute hydrochloric acid, water, dried with sodium sulfate and finally evaporated to dryness. The crude product was chromatographed as described in example 1 to yield 0.20 g of pure 6-methylenandrosta-1,4-diene-3,17-dione, m.p. 188°–191° C.

By proceeding analogously, the following compounds can be prepared:
1-methyl-6-methylenandrosta-1,4-diene-3,17-dione,
Found: C 81.18; H 8.37. $C_{21}H_{26}O_2$ requires: C 81.25; H 8.44;
1-ethyl-6-methylenandrosta-1,4-diene-3,17-dione, Found: C 81.32; H 8.62. C$_{22}$H$_{28}$O$_2$ requires: C 81.44; H 8.70;

4-methyl-6-methylenandrosta-1,4-diene-3,17-dione,
Found: C 81.15; H 8.32. C$_{21}$H$_{26}$O$_2$ requries: C 81.25; H 8.44;

4-ethyl-6-methylenandrosta-1,4-diene-3,17-dione;
6-ethyldenandrosta-1,4-diene-3,17-dione;
6-propylidenandrosta-1,4-diene-3,17-dione, and
1-methyl-6-ethylidenandrosta-1,4-diene-3,17-dione.

EXAMPLE 3

A solution of 4,5-epoxy-6-methylenandrost-1-ene-3,17-dione (1.0 g) in glacial acetic acid (10 ml) was treated with gaseous hydrogen chloride for 30 min at room temperature The precipitate was filtered off, washed with diethyl ether, dried and chromatographed on silica gel using hexane/ethyl acetate to yield 0.8 g of pure 4-chloro-6-methylenandrosta-1,4-diene-3,17-dione.

Found: C 72.40, H 6.91, Cl 10.53; C$_{20}$H$_{23}$ClO$_2$ requires: C 72.61, H 7.01, Cl 10.72.

N.M.R. δp.p.m.: 0.84 (3H, s); 1.24 (3H, s); 5.13 (1H, s); 5.43 (1H, s); 6.37 (1H, d); 7.08 (1H, d).

MS (m/z): 330.

Following the above reported procedure and starting from the appropriate 4,5-epoxy derivative and using the appropriate gaseous hydrohalic acid, the following compounds can be prepared:

4-bromo-6-metyylenandrosta-1,4-diene-3,17-dione,
Found: C 63.90; H 6.03; Br 21.15. C$_{20}$H$_{23}$BrO$_2$ requires: C 64.00; H 6.18; Br 21.29;

4-fluoro-6-methylenandrosta-1,4-diene-3,17-dione,
Found: C 76.35; H 7.34; F 6.01. C$_{20}$H$_{23}$FO$_2$ requires: C 76.41; H 7.37; F 6.04.

4-chloro-1-methyl-6-methylenandrosta-1,4-diene-3,17-dione;
4-bromo-1-methyl-6-methylenandrosta-1,4-diene-3,17-dione;
4-fluoro-1-methyl-6-methylenandrosta-1,4-diene-3,17-dione,
Found: C 76.75; H 7.62; F 5.71. C$_{21}$H$_{25}$FO$_2$ requires: C 76.80; H 7.67; F 5.79;

4-chloro-6-ethylidenandrosta-1,4-diene-3,17-dione;
4-bromo-6-ethylidenandrosta-1,4-diene-3,17-dione, and
4-fluoro-6-ethylidenandrosta-1,4-diene-3,17-dione.

EXAMPLE 4

A solution of 4,5-epoxy-6-methylenandrost-1-ene-3,17-dione (1.0 g) in diethyl ether (100 ml) was treated with boron trifluoride etherate (1.4 ml) for 3 hours at room temperature. Then the solution was washed with 5% sodium carbonate solution, water, dried (Na$_2$SO$_4$) and evaporated in vacuo. The residue was dissolved in pyridine (20 ml) and 0.4 ml of thionyl chloride were added at 0° C. After 5 minutes water was added and the product isolated with ether. The ether extracts were washed with 2N hydrochloric acid, water, dried (Na$_2$SO$_4$) and evaporated. The resulting raw product was chromatographed on silica gel using hexane/ethyl acetate as eluant to yield 0.6 g of pure 4-fluoro-6-methylenandrosta-1,4-diene-3,17-dione.

Found: C 76.30; H 7.35; F 5.91; C$_{20}$H$_{23}$FO$_2$ requires: C 76.40; H 7.37; F 6.04.

The following compounds can be prepared using the above mentioned method:

4-fluoro-1-methyl-6-methylenandrosta-1,4-diene-3,17-dione;
4-fluoro-6-ethylidenandrosta-1,4-diene-3,17-dione.

EXAMPLE 5

6-methylenandrost-4-ene-3,17-dione (5 g) was dissolved in 200 ml of methanol and cooled to 0° C. Thereupon ice cold 36% H$_2$O$_2$ (17 ml) and 2% NaOH (9 ml) was added. The mixture was stirred for 1 hour, allowed to stand at 5° C. for 20 hours and then poured into 1400 ml of ice water with vigorous stirring, the product was filtered, washed with water and dried to give 4.2 g (80%) of 4,5-epoxy-6-methylenandrosta-3,17-dione [α/β-epoxide mixture]; N.M.R. δp.p.m.: 0.90 (3H, s); 0.97 (3H, s); 3.52 (1H, s); 4.92 (1H, broad); 5.06 (1H, broad).

4,5-Epoxy-6-methylenandrosta-3,17-dione (3 g) and dichlorodicyanobenzoquinone (1.7 g) dissolved in 60 ml of anhydrous dioxane were heated to reflux for about 15 hours. The cooled solution was filtered through alumina and the solvent evaporated in vacuo. The residue was taken up with ethylacetate, the organic layer washed with water, dried and the solvent removed under vacuum. The crude product was chromatographed on silica gel using hexane/ethylacetate 10–40% to yield 1.5 g of pure 4,5-epoxy-6-methylenandrost-1-ene-3,17-dione; N.M.R. δp.p.m.: 0.93 (3H, s); 1.13 (3H, s); 3.71 (1H, d); 5.03 (2H, m); 5.86 (1H, d); 6.78 (1H, d).

Following the above described procedure and using the appropriate 6-alkylidenandrost-4-ene-3,17-dione the following compounds can be prepared:

1-methyl-4,5-epoxy-6-methylenandrost-1-ene-3,17-dione;
1-ethyl-4,5-epoxy-6-methylenandrost-1-ene-3,17-dione;
4,5-epoxy-6-ethylidenandrost-1-ene-3,17-dione;
1-methyl-4,5-epoxy-6-ethylidenandrost-1-ene-3,17-dione; and
1-ethyl-4,5-epoxy-6-ethylidenandrost-1-ene-3,17-dione.

EXAMPLE 6

A solution of lithium dimethyl copper was prepared under nitrogen by the addition of 1.6M ethereal methyl lithium to a slurry of cuprous iodide in anhydrous ether at 0° C. The solution was stirred at 0° C. for 20 min and then 5α-androst-1-ene-3,17-dione in anhydrous tetrahydrofuran was added over a 20-minute period and stirred for an additional 30 min. The mixture was poured onto a saturated aqueous ammonium chloride solution, then benzene was added and the resulting mixture was rapidly filtered through diatomaceous earth. The organic layer was washed with aqueous ammonium chloride, water, dried over magnesium sulfate and evaporated to dryness. The residue was chromatographed on silica gel using hexane/ethylacetate 10–20% to give 1β-methyl-5α-androsta-3,17-dione; I.R. (KBr): 1710 cm$^{-1}$ (3-oxo), 1740 cm$^{-1}$ (17-oxo).

To a solution of 1β-methyl-5α-androsta-3,17-dione (3.025 g, 10 mmol) in glacial acetic acid (100 ml) a solution of bromine (1.60 g, 10 mmol) in glacial acetic acid (30 ml) containing one drop of 47% HBr was added dropwise at 20°–25° C. with vigorous stirring. The bromine was consumed after 20 min.

The solution was poured into water and the resulting precipitate was collected, washed well with water and dried in vacuo to yield 3.82 g (100%) of crude 4-bromo-1β-methyl-5α-androsta-3,17-dione; I.R. (KBr): 1740 cm$^{-1}$ (3-oxo, 17-oxo).

A solution of the crude bromo-compound obtained as above in dimethylformamide (100 ml) was stirred with dried lithium chloride (7 g) at 140°–150° C. After cooling the solution was poured into water and the resulting oily product was extracted with ether. The organic layer was washed with 10% hydrochloric acid and water, dried and then evaporated in vacuo. The residue was chromatographed on silica gel using hexane/ethylacetate 10-30% to yield 2.4 g (80%) of 1β-methyl-androst-4-ene-3,17-dione; I.R. (KBr): 1620 ($\Delta^4$), 1660 (3-oxo), 1735 cm$^{-1}$ (17-oxo).

A mixture of sodium acetate (1 g), absolute chloroform (30 ml), formaldehyde-diethylacetal (30 ml, 0.24 mol), phosphoryl chloride (3.8 ml, 0.04 mol), and 1β-methyl-androst-4-ene-3,17-dione (0.811 g, 2.7 mmol) was stirred at reflux for about 7 hours, i.e. until the starting material had disappeared. The suspension was allowed to cool and under vigorous stirring a saturated sodium carbonate solution was added dropwise until the pH of the aqueous layer became alkaline (~1 hour). The organic layer was separated, neutralized with water, and dried with sodium sulfate. After concentration under reduced pressure the oily residue was purified by chromatography on silica gel using hexane/ethylacetate as eluent. Thus the pure 1β-methyl-6-methylenandrost-4-ene-3,17-dione was obtained in 60% yield (0.195 g); I.R. (KBr): 3100 (6=$CH_2$), 1735 (17-oxo), 1680 (3-oxo), 1630, 1660 cm$^{-1}$ ($\Delta^4$ and 6=$CH_2$).

By proceeding analogously the following compounds can be prepared:
1β-ethyl-6-methylenandrost-4-ene-3,17-dione;
1β-methyl-6-ethylidenandrost-4-ene-3,17-dione; and
1β-ethyl-6-ethylidenandrost-4-ene-3,17-dione.

EXAMPLE 7

A solution of androst-4-ene-3,17-dione in t-butanol was heated to boiling and added to a boiling solution of potassium t-butoxide in t-butanol. Methyl chloride in t-butanol was added slowly. The solution was cooled, acidified with concentrated hydrochloric acid, and diluted with water. The excess t-butanol was removed under vacuum and the aqueous layer extracted with ethylacetate. The combined extracts were washed with water, dried over magnesium sulfate and evaporated in vacuo. The residue was chromatographed on silica gel and eluted with hexane/ethylacetate. The eluant was evaporated and the residue crystallized from ether to yield 4-methylandrost-4-ene-3,17-dione; I.R. (KBr): 1735 (17-oxo), 1660 (3-oxo), 1620 cm$^{-1}$ ($\Delta^4$).

Alternatively, a mixture of androst-4-ene-3,17-dione, thiophenol, 40% aqueous formaldehyde, triethylamine and ethanol was heated under reflux for a period of about 48 hours. The cooled solution was poured onto an aqueous sodium hydroxide solution and the product isolated by ether extraction. The ether extracts were washed with water and dried over magnesium sulfate. The resulting residue was triturated with hexane to remove any condensation by-product derived from the thiophenol and formaldehyde. The 4-phenylthiomethylandrost-4-ene-3,17-dione so obtained was desulfurized by dissolving in acetone and adding to a suspension of Raney Nickel in refluxing acetone. The mixture was refluxed for about 5 hours under stirring. The hot solution was filtered and the catalyst washed with boiling ethanol and water. The combined filtrates were concentrated under vacuum whereupon the product separated as a solid mass. Recrystallization from acetone/hexane yielded 4-methylandrost-4-ene-3,17-dione. A mixture of sodium acetate (1 g), absolute chloroform (30 ml), formaldehyde diethyl acetal (30 ml, 0.24 mol), phosphoryl chloride (3.8 ml, 0.04 mol), and 4-methylandrost-4-ene-3,17-dione (0.81 g, 2.7 mmol) was refluxed for about 7 hours, i.e. until the starting material has disappeared. The suspension was allowed to cool and under vigorous stirring a saturated sodium carbonate solution was added dropwise until the pH of the aqueous layer became alcaline (~1 hour). The organic layer was separated, neutralized with water, and dried over sodium sulfate. After concentration under reduced pressure the oily residue was purified by chromatography on silica gel using hexane/ethylacetate as eluent. Thus the pure 4-methyl-6-methylenandrost-4-ene-3,17-dione was obtained in 60% yield; I.R. (KBr): 3080 (6=$CH_2$), 1735 (17-oxo), 1665 (3-oxo), 1635, 1595 cm$^{-1}$ ($\Delta^4$ and 6=$CH_2$).

By proceeding analogously, the following compounds can be prepared:
1β,4-dimethyl-6-methylenandrost-4-ene-3,17-dione;
1β-ethyl-4-methyl-6-methylenandrost-4-ene-3,17-dione;
1β,4-diethyl-6-methylenandrost-4-ene-3,17-dione;
4-methyl-6-ethylidenandrost-4-ene-3,17-dione; and
1β,4-dimethyl-6-ethylidenandrost-4-ene-3,17-dione.

EXAMPLE 8

Tables each weighing 0.150 g and containing 25 mg of the active substance, can be manufactured as follows;
Composition (for 10000 tablets)
6-methylenandrosta-1,4-diene-3,17-dione; 250 g
Lactose: 800 g
Corn starch: 415 g
Talc powder: 30 g
Magnesium stearate: 5 g
The 6-methylenandrosta-1,4-diene-3,17-dione, the lactose and half the corn starch are mixed; the mixture is then forced throught a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate is added, carefully mixed and processed into tablets.

EXAMPLE 9

Capsules, each dosed at 0.200 g and containing 20 mg of the active substance can be prepared.
Composition for 500 capsules:
6-methylenandrosta-1,4-diene-3,17-dione: 10 g
Lactose: 80 g
Corn starch: 5 g
Magnesium stearate: 5 g
This formulation is encapsulated in two-piece hard gelatin capsules and dosed at 0.200 g for each capsule.

We claim:

1. A compound of general formula (I)

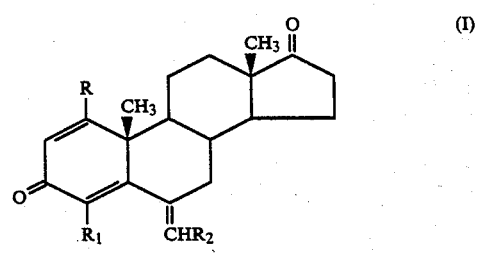

wherein each of R and $R_2$, independently, is hydrogen or $C_1$-$C_6$ alkyl and $R_1$ is hydrogen, halogen or $C_1$-$C_6$ alkyl.

2. A compound of formula (I), according to claim 1, wherein

R is hydrogen or $C_1$-$C_4$ alkyl;
$R_1$ is hydrogen, fluorine, chlorine or $C_1$-$C_4$ alkyl; and
$R_2$ is hydrogen or $C_1$-$C_4$ alkyl.

3. A compound of formula (I), according to claim 1, wherein

R is hydrogen, methyl or ethyl;
$R_1$ is hydrogen, fluorine or chlorine and
$R_2$ is hydrogen.

4. A pharmaceutical composition containing a suitable carrier and/or diluent and, as an active principle, a therapeutically effective amount of a compound of claim 1, or a pharmaceutically acceptable salt thereof.

5. A pharmaceutical composition, suitable for the treatment of advanced hormone-dependent breast, pancreatic, endometrial or ovarian cancers, comprising, as an active principle, a therapeutically effective amount of a compound of claim 1, in association with a suitable carrier and/or diluent.

6. A pharmaceutical composition, suitable for the treatment of prostatic hypertrophy or prostatic hyperplasia, comprising, as an active principle, a therapeutically effective amount of a compound of claim 1, in association with a suitable carrier and/or diluent.

7. A method for the treatment of advanced hormone-dependent breast, pancreatic, endometrial or ovarian cancer comprising administering patients in need of such treatment an effective amount of a compound of claim 1.

8. A method for the treatment of prostatic hypertrophy or prostatic hyperplasia comprising administering to patients in need of such treatment an effective amount of a compound of claim 1.

* * * * *

UNITED STATES PATENT AND TRADEMARK OFFICE
CERTIFICATE OF CORRECTION

PATENT NO. : 4,904,650

DATED : February 27, 1990

INVENTOR(S) : BUZZETTI et al

It is certified that error appears in the above-identified patent and that said Letters Patent is hereby corrected as shown below:

On the cover page, Item [73], "Farmitalia Carlo Erba S.p.A." should read --Farmitalia Carlo Erba S.r.l.--.

Signed and Sealed this

Third Day of September, 1991

Attest:

HARRY F. MANBECK, JR.

*Attesting Officer*  *Commissioner of Patents and Trademarks*